United States Patent [19]

Guegan et al.

[11] Patent Number: 5,109,866
[45] Date of Patent: May 5, 1992

[54] ARTIFICIAL PANCREAS

[75] Inventors: Alain Guegan, Lorient; Jules Gy, Pace; Jean-Pierre Hespel, Rennes; Philippe Rouyer, Pace, all of France

[73] Assignee: Societe d'Applications des Techniques Photoniques, France

[21] Appl. No.: 490,610

[22] PCT Filed: Jul. 22, 1989

[86] PCT No.: PCT/FR89/00380
 § 371 Date: Mar. 21, 1990
 § 102(e) Date: Mar. 21, 1990

[87] PCT Pub. No.: WO90/00909
 PCT Pub. Date: Feb. 8, 1990

[30] Foreign Application Priority Data

July 21, 1988 [FR] France ............... 88-10036

[51] Int. Cl.$^5$ ............................................. A61B 17/3
[52] U.S. Cl. ........................... 128/771; 128/637; 604/66; 422/63
[58] Field of Search ............... 604/27—31, 604/48-53, 65-67, 246; 128/632, 633, 636, 637, 664, 665, 771, DIG. 13; 364/413.07, 413.09; 422/63-65, 68.1

[56] References Cited

U.S. PATENT DOCUMENTS

| 3,994,593 | 11/1976 | Kato et al. | 356/203 |
|---|---|---|---|
| 4,206,755 | 6/1980 | Klein | 604/28 |
| 4,637,403 | 1/1987 | Garcia et al. | 128/770 |
| 4,717,546 | 1/1988 | Barnett | 422/63 |
| 4,790,979 | 12/1988 | Terminiello et al. | 422/56 |
| 4,820,491 | 4/1989 | Khoja et al. | 422/63 |
| 4,937,050 | 6/1990 | Meinecke et al. | 422/68.1 |
| 4,959,196 | 9/1990 | Moisson | 422/82.05 |
| 5,035,704 | 7/1991 | Lambert et al. | 606/182 |

FOREIGN PATENT DOCUMENTS

| 0064691 | 11/1982 | European Pat. Off. . |
| 2849367 | 5/1979 | Fed. Rep. of Germany . |
| 222124 | 5/1985 | German Democratic Rep. . |

Primary Examiner—Stephen C. Pellegrino
Assistant Examiner—Steven J. Shumaker
Attorney, Agent, or Firm—Skjerven, Morrill, MacPherson, Franklin & Friel

[57] ABSTRACT

The artificial pancreas comprises a unit for automatic and periodical withdrawal of blood samples from the body of a patient (M), a unit for measuring the glycemia of this sample, a unit (8) for injecting insulin or glucose, and a unit (U) for calculation and data processing in order to determine the amount of insulin or glucose which is to be administered to the patient as a function of the glucose level measured by the measurement unit, and to control consequently the injection unit (8). This artificial pancreas is characterized in that the measurement of the glycemia is effected by reading the color of a strip reacting to glycemia, the measurement unit comprising to this effect: a) a strip distribution station (3); b) a station (4) for depositing a blood droplet on the strip; c) a station (5) for wiping the strip; d) a station (6) for optical reading of the color taken by the strip; e) a station (7) for removing the strip; f) a transportation device (1, 2) for conveying the strips individually from station to station.

11 Claims, 6 Drawing Sheets

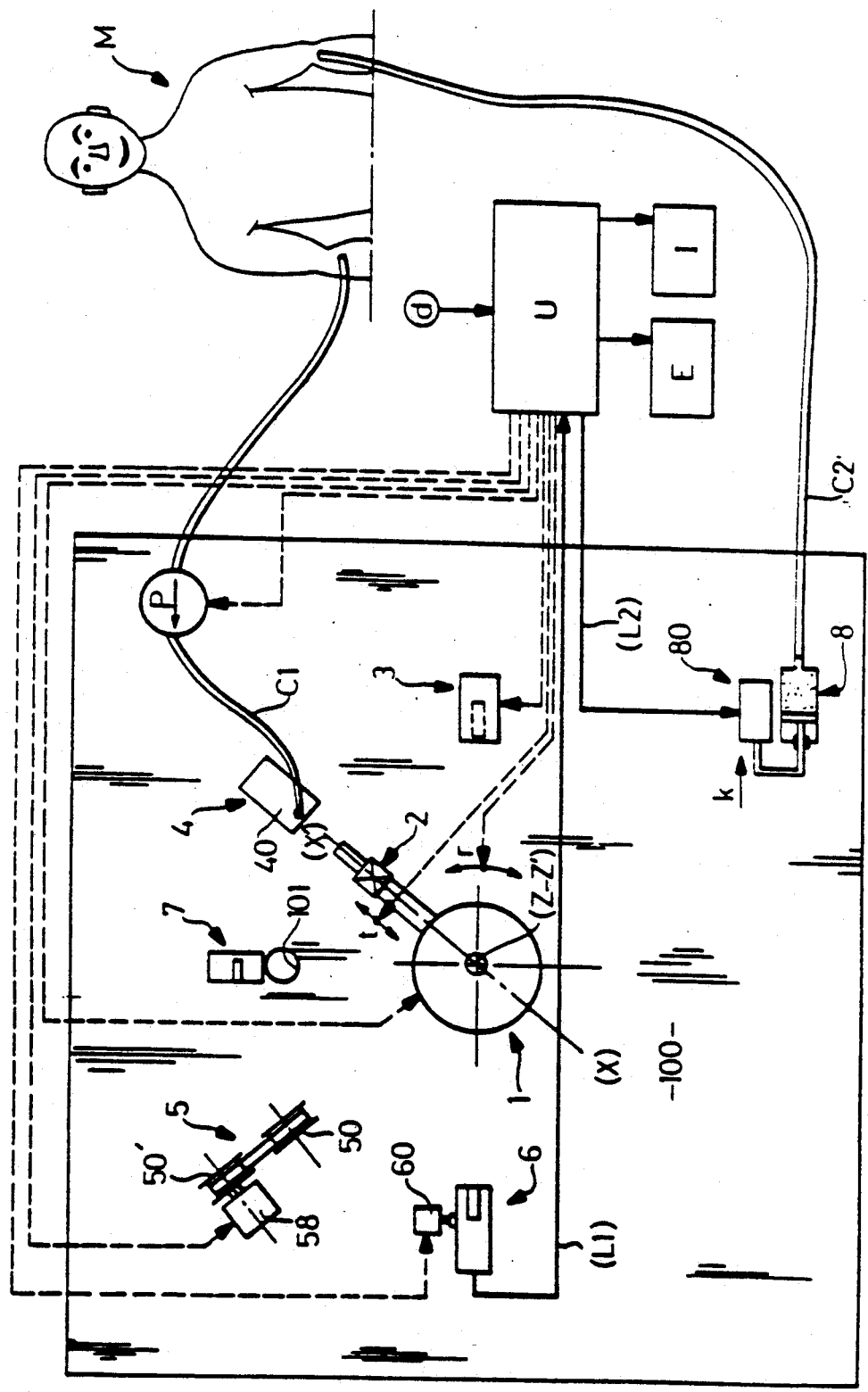

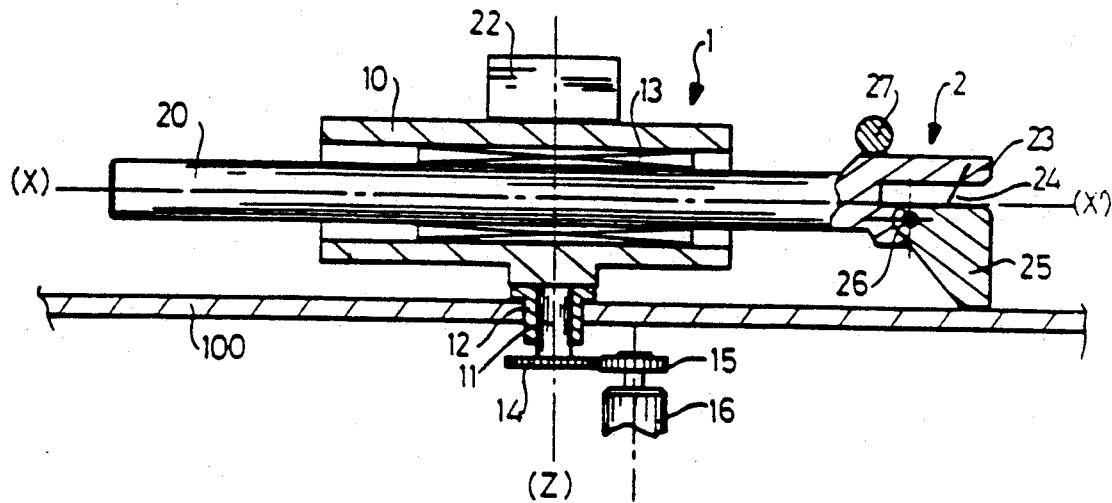
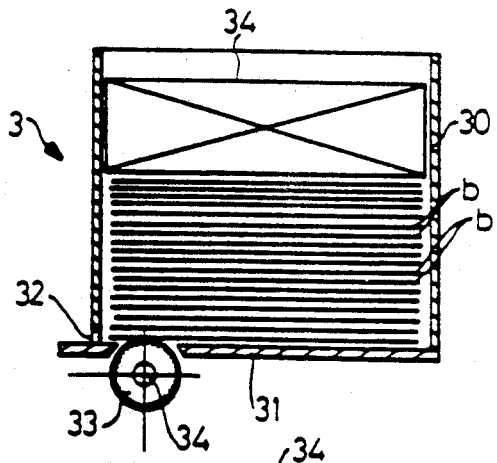
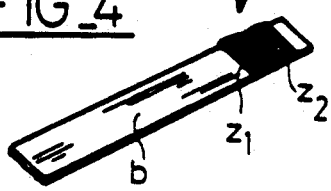
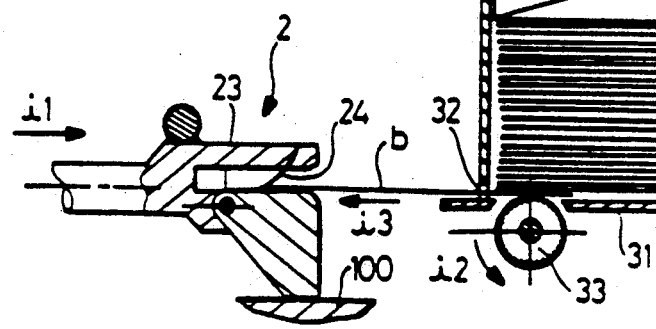

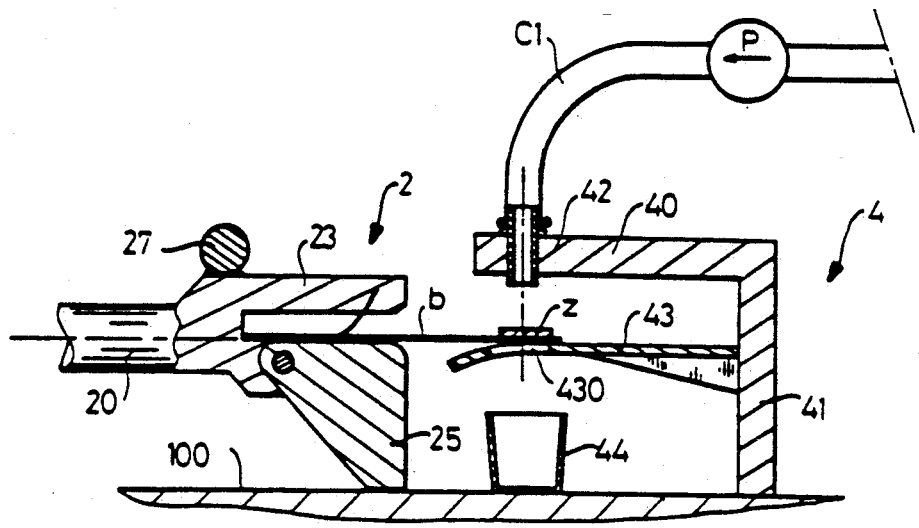
FIG_6
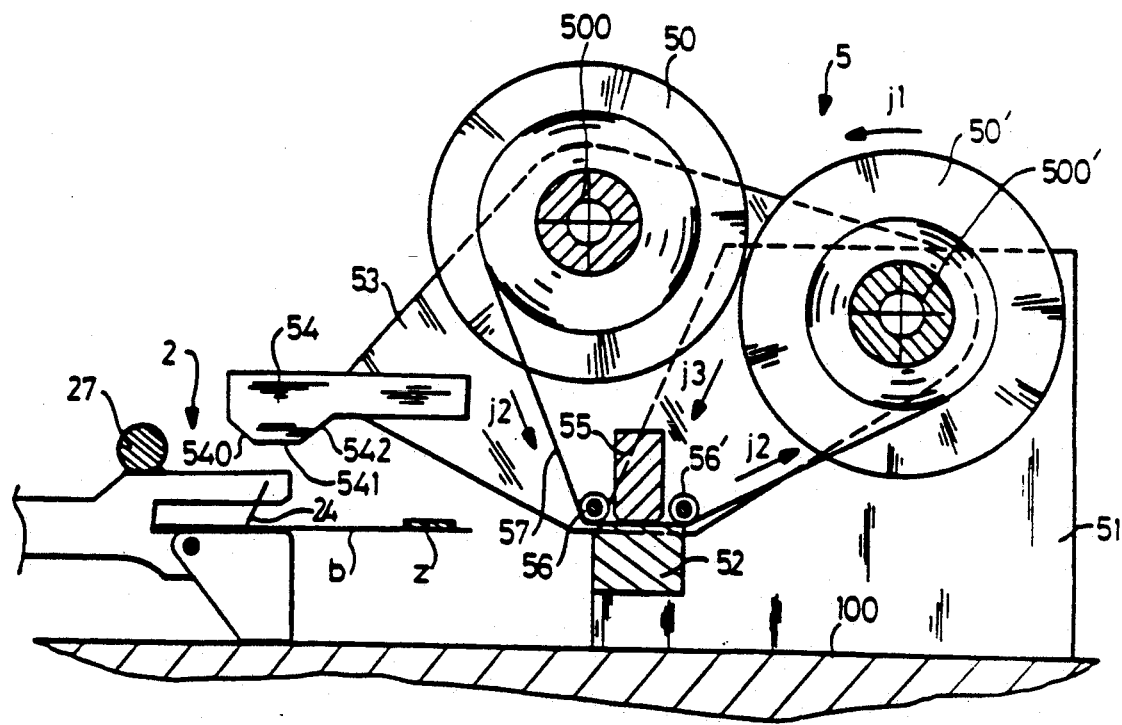
FIG_7

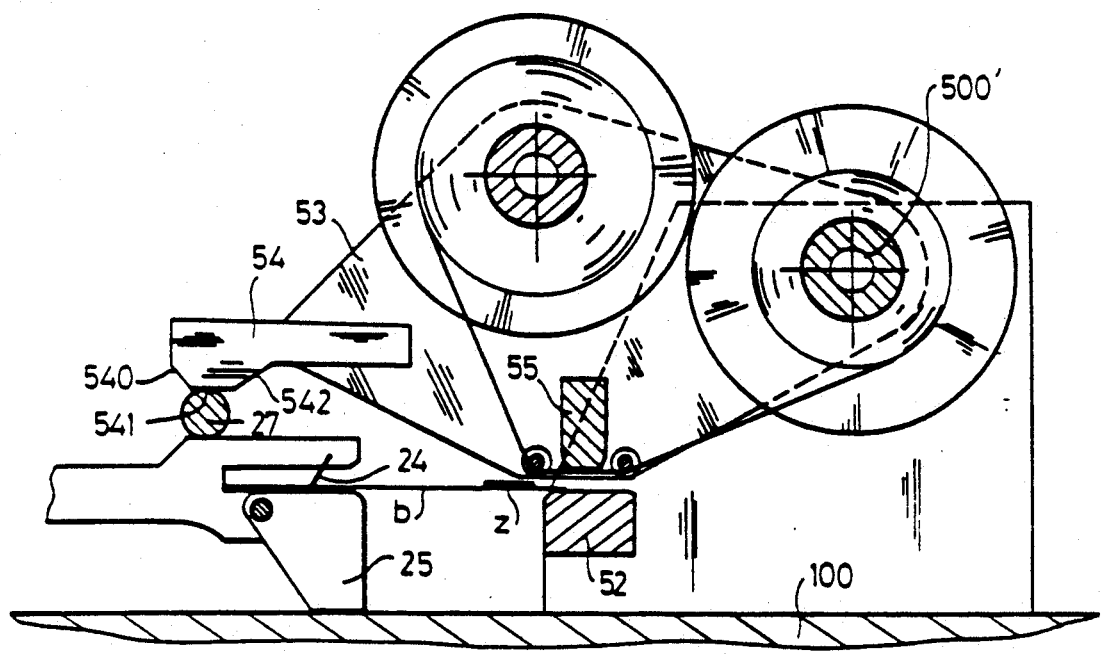
FIG_8
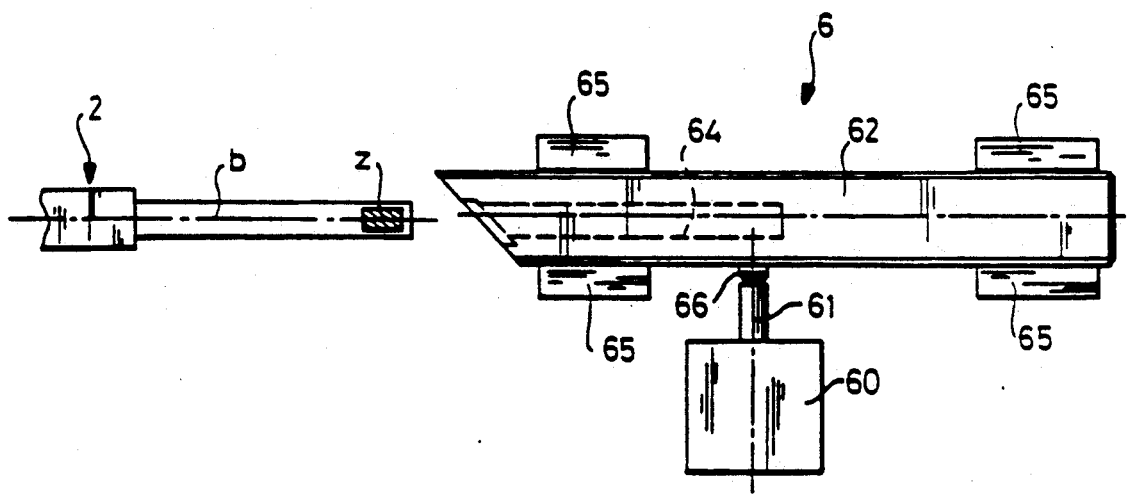
FIG_9

FIG_10
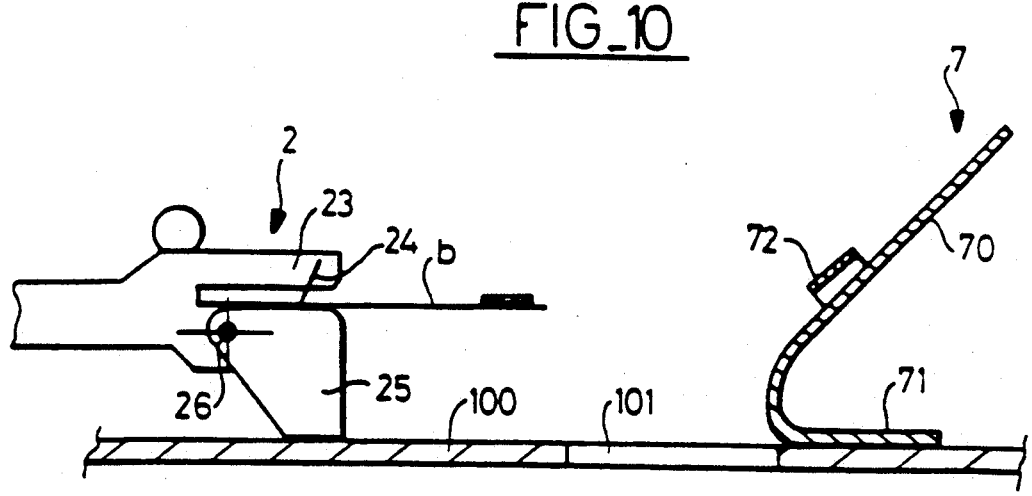
FIG_11
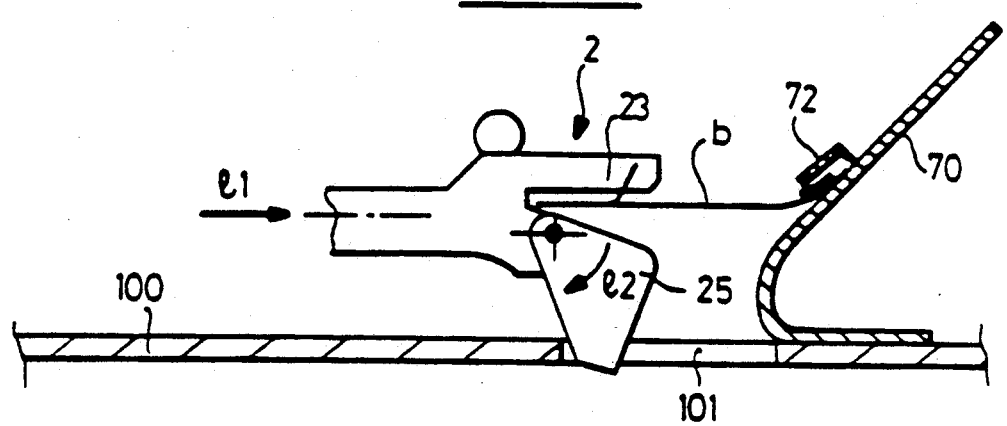
FIG_12
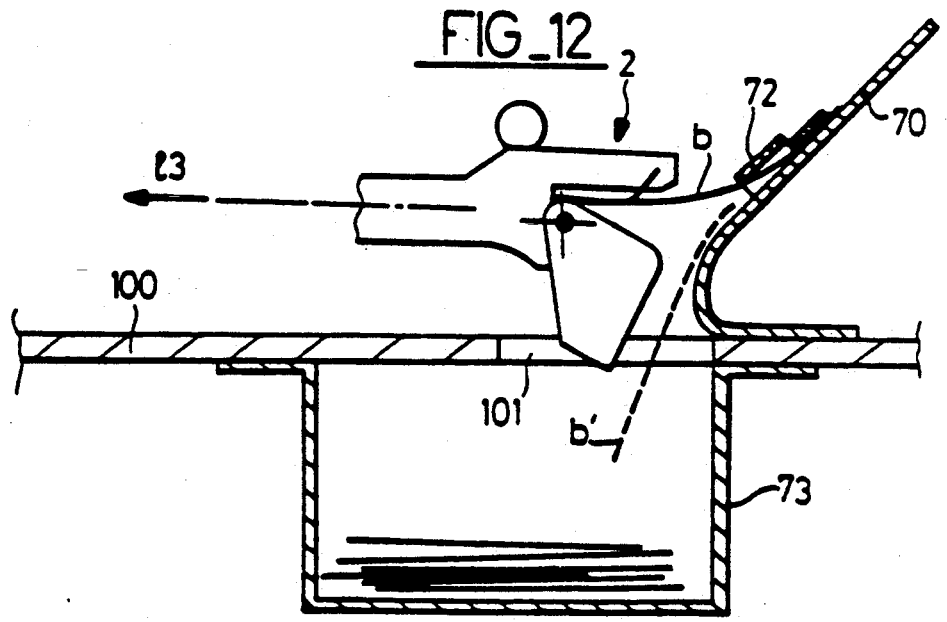

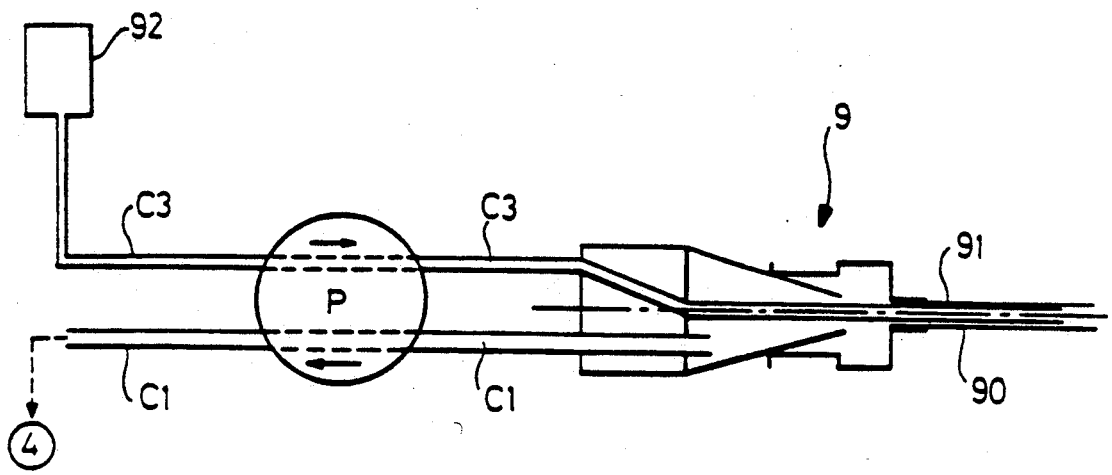
FIG_13
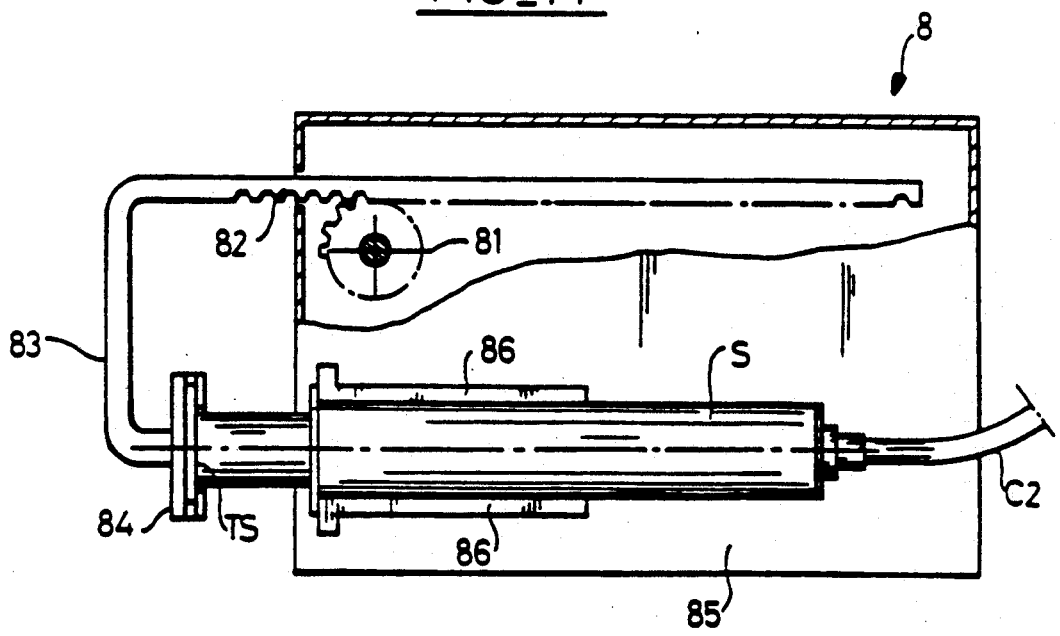
FIG_14

ARTIFICIAL PANCREAS

The present invention relates to an artificial pancreas.

It is known that the pancreas has a twin function. The first is a digestive function, by means of the acini which it contains, the pancreas secreting digestive enzymes into the duodenum. The second is a regulatory function, the pancreas stabilizing the level of glucose present in the blood by means of the islets of Langherhans which secrete at least four hormones.

The role of the pancreas is therefore to stabilize the blood glycemia (sic) (blood glucose level). It is this function to which the present invention relates. The pancreas achieves this by means of several hormones, of which the main one is insulin. Whatever the glucose absorbed, the blood glycemia (sic) should not vary greatly about an average value, which is of the order of 0.9 g/l (grams per liter); this is the case in nondiabetic subjects.

In the case of a healthy subject, the glycemia oscillates between 0.5 and 1.5 g/l depending on the subject and the time of day.

A diabetic is a person whose blood glucose level is not stabilized by the organ. When there is diabetes, the glycemia can exceed 1.5 g/l (hyperglycemia) or be less than 0.5 g/l (hypoglycemia).

The artificial pancreas which is the subject of the invention is an extracorporeal device (not intended to be implanted) which is designed to return the glucose level (glycemia) to a normal value by means of programmed injection of insulin and/or glucose The artificial pancreas is presented as a closedloop system in which the glucose level is the variable to be controlled. The system functions by injecting insulin or glucose, whose delivery rate has been calculated on the basis of the glycemia of a blood sample, this by means of an algorithm previously defined by therapists and integrated in the program.

This artificial pancreas is not designed to be used permanently on a diabetic, but to be used temporarily, for example for a period of the order of one day, for examining a patient in order to establish his requirements and his reactions to the insulin or glucose injection, this in order to be able to determine with accuracy the treatment which is suitable for him and which will be prescribed subsequently for him.

In the known devices of this type, the measurement of the glycemia is generally carried out by the traditional method (wet-state chemistry) which is lengthy, laborious, and requires qualified personnel; more modern methods have been proposed, particularly in document EP-A-098 592, which proposes an artificial pancreas in which the measurement of the glycemia is carried out by electro-polarographic means, which makes it possible to operate automatically; however, this equipment appears to be relatively sophisticated, very expensive and difficult to use.

The present invention aims to resolve these problems by proposing a device of the type mentioned, whose unit for measuring the glycemia is strong and durable, relatively inexpensive, gives accurate and reliable results, and lends itself to complete automation of the operation. This result is essentially achieved by virtue of the fact that the measuring technique employed is a proven technique in dry-state chemistry, consisting in reading by optical means the color taken by the glycemia-reactive zone of a strip, on which zone the blood sample has previously been deposited in the form of a droplet. This type of measurement is currently carried out periodically by diabetics, who can thus check their glycemia level themselves.

It is for this reason that the main aim of the invention is to integrate this proven measurement technique in an artificial pancreas, and this by automatizing the procedure.

The artificial pancreas which is the subject of the invention comprises a unit for automatic and periodical withdrawal of blood samples from the body of a patient, a unit for measuring the level of glucose present in this sample (glycemia), a unit for injection of a dose of insulin or glucose into the body of the patient, and a unit for calculation and data processing able to determine the amount of insulin or glucose which is to be administered to the patient as a function of the glucose level measured by the measurement unit, and to control the injection unit in a corresponding manner. This artificial pancreas is characterized in that the measurement of the glycemia is carried out by reading of the color of the zone of a strip which is reactive to glycemia, the measurement unit comprising to this effect:

a) a strip distribution station;
b) a station in which a blood droplet supplied by the said sampling unit is deposited on the reactive zone of a strip;
c) a station for wiping the zone;
d) a station for optical reading of the color taken by this zone;
e) a station for removing the strip;
f) a transportation device for conveying the strips individually from station to station.

Moreover, according to a certain number of advantageous (but non-limiting) characteristics:

the transportation device comprises a pincer whose jaws are designed to grip and retain a strip, the pincer being mounted movable in translation along a substantially horizontal axis in a rotatory turret of vertical axis;

the strip distribution station comprises a container in which the strips are stacked horizontally under a certain pressure, a rotatory drive knurled wheel provided at the level of the base of this container being designed to remove from the container, through an appropriate opening, the bottom strip in the stack;

one of the jaws of the pincer is provided with a small elastic tongue for blocking the strip in order to prevent it from coming out of the pincer;

the station in which a blood droplet is deposited on the reactive zone of the strip comprises a support plate passed through by a small conduit for delivery of the blood, and an element for bearing of the strip and arranged at the base of the small delivery conduit;

the wiping station comprises a frame equipped with a pair of reels for distributing and receiving respectively a band of absorbent paper, means being provided for driving at least one of the reels in rotation over a certain course, and thereby to unreel the band;

the band is guided by rollers so as to pass between a lower pressing block and an upper pressing block, the reactive zone of the strip taking up a position between these two blocks, with the band applied against its reactive zone;

the band of absorbent paper and the upper pressing block are borne by a plate which is articulated on the frame about a horizontal axis, this plate being integral with a cam for cooperating with a control member equipped on the pincer for bringing about the temporary lifting of the upper block and the band during the positioning of the reactive zone of the strip between the two blocks, and during withdrawal of this strip;

the station for optical reading of the color taken by the reactive zone of the strip comprises a reading casing provided with a slot turned towards the transporter device and oriented in such a way as to be situated in the trajectory of the strip;

the pincer comprises a fixed upper jaw and a lower jaw articulated about a horizontal axis, the closure of the pincer being normally ensured by this lower jaw bearing on the assembly deck for the set of stations;

the station for removal of the strip comprises an inclined plate which is provided with a small tongue for retaining the strip, this plate being arranged in the proximity of an opening made in the assembly deck, this opening on the one hand causing the pincer to open by means of the swinging of the lower jaw and on the other hand permitting the passage of the removed strips, advantageously towards a receiving container.

Other characteristics and advantages of the invention will emerge from the description and from the attached drawings which illustrate a preferred embodiment thereof, designed for the injection of insulin.

In these drawings:

FIG. 1 is a general schematic view of the whole of the artificial pancreas system which is the subject of the invention;

FIG. 2 shows a side view and longitudinal cutaway of the transportation device;

FIG. 3 is a transverse cutaway of the device in FIG. 2;

FIG. 4 shows a perspective view of a reactive strip;

FIG. 5 shows the strip distribution station;

FIG. 5a is a similar view to FIG. 5, showing the manner in which the distribution of a strip is effected;

FIG. 6 is a schematic side view of the station in which a droplet of blood is deposited on the reactive zone of a strip;

FIG. 7 is a schematic side view of the wiping station;

FIG. 8 is a similar view to FIG. 7, which shows the way in which the wiping head is lifted during the positioning of a strip in this station;

FIG. 9 is a schematic plan view of the station for optical reading of the color taken by the reactive zone of a strip;

FIG. 10 is a schematic view of the station for removing the used strips, FIGS. 11 and 12 being similar views showing several steps in the removal procedure;

FIG. 13 is a schematic view of the double catheter permitting withdrawal of a sample of heparinated blood;

FIG. 14 is a schematic plan view of the syringe-push device.

FIG. 1 is a general view of the artificial pancreas according to the invention. This device comprises an assembly base or deck 100 on which there are mounted the various stations constituting the unit for measuring the glycemia, the device for transporting strips from station to station, and the unit for injecting insulin. The patient (diabetic subject) is designated by the reference (M). A unit for automatic and periodical withdrawal of blood samples from the body of this patient comprises a catheter ($C_1$) which is inserted in one of the arms of the patient in order to withdraw blood therefrom, the pumping of the latter being carried out by a pump (P), for example of the peristaltic type.

The unit for injecting a dose of insulin comprises a syringe 8 containing a certain amount of insulin, which syringe is connected via a second catheter ($C_2$) to the other arm of the patient (M). The syringe is actuated by a syringe-push 80 of known type capable of delivering a predetermined dose of insulin by displacement of the syringe plunger over a certain well-defined course (arrow k, FIG. 1).

On the deck 100, which is a stable metallic plate, there are attached by appropriate means, such as screws for example, the various stations constituting the measurement unit. These stations are:

a strip distribution station 3, a station 4 at which the first catheter ($C_1$) empties, whose role is to deposit a blood droplet on the reactive zone of a strip;

a station 5 for wiping the reactive zone of the strip;

a station 6 for optical reading of the color taken by the reactive zone;

a station 7 for removing the strip.

It will be noted that the station 4 is provided with a horizontal plate 40 to which there is fixed the downstream end of the catheter ($C_1$); it will be noticed that an opening 101' passing through the deck 100 is provided in front of the removal station 7; it will also be noticed that the wiping station 5 comprises two reels 50, 50' of which one (50') is driven in rotation by appropriate means 58 such as an electrical geared motor; finally, it will be noted that the reading station 6 is equipped with an actuating member, such as a solenoid 60, designed to act on a switch on the reading device.

Mounted in the central part of the deck 100 is a transportation device which comprises a rotating part 1 capable of turning about a vertical axis (Z—Z'), this part bearing a pincer 2 which is movable in translation following a horizontal axis (parallel to the deck 100), radially relative to the axis (Z—Z'). This axis, along which the pincer 2 moves, is designated (X—X').

The ability of the transportation device to rotate, which corresponds to the pivoting of the part 1, in one direction or the other about the axis (Z—Z') is symbolized by the double arrow (r), while the possibility of translation of the pincer 2 along the axis (X—X') is symbolized by the double arrow (t).

The various stations 3, 4, 7, 5 and 6 are arranged essentially in an imaginary cirle of axis (Z—Z'). Each of these stations is therefore accessible to the pincer 2 which can transport a strip there, after rotation of the part 1 about an appropriate angle and translation of the pincer 2 in the direction of the station concerned.

The reference (U) has been used to designate a unit for calculation and data processing which is able to determine the amount of insulin which is to be administered to the patient as a function of the glucose level measured by the measurement unit. It is possible to introduce into this unit, by means of an appropriate keyboard, data (d) relating to the patient (M). The determination of the amount of insulin desired is carried out on the basis of an appropriate algorithm, previously developed by the therapist. This unit for calculation and data processing is advantageously connected to a display screen (E) and to a printer (I). The main data it receives is the glycemia reading carried out at station 6, the corresponding electrical signals being transmitted via a line ($L_1$). After processing this data, the unit (U) sends to the unit for insulin injection a suitable order corresponding to the dose which is to be administered to the patient (M) via the catheter ($C_2$); this order passes via a branch designated ($L_2$).

Similarly, using means which are within the scope of the person skilled in the art and which will not be elaborated upon here, the unit for calculation and data processing will control, in accordance with a sequence and delay times which are well defined, the start-up of the transporter 1, 2 and that of the various stations 3, 4, 5, 6, 7 of the measurement unit.

FIGS. 2 and 3 show the transporter. As has already been mentioned, the latter comprises a part 1 able to turn about a vertical axis (Z—Z') and a part 2 forming a pincer able to move in translation along an axis (X—X') (an axis which is itself movable about the abovementioned axis (Z—Z')).

The part 1 comprises a main body or turret 10 which is borne on a shaft 11 of axis (Z—Z') guided in rotation in a sleeve 12 which passes through the deck 100. Under the deck, the shaft 11 bears a pinion 14 which is in engagement with another pinion 15 mounted at the output of a small electrical geared motor 16. The rotation of the geared motor 16 in one direction or the other results in the corresponding rotation of the turret 10 about the axis (Z—Z'). The geared motor 16 is mounted under the deck 100 by suitable means which have not been shown for the simple purpose of simplification.

The part 2 forming a pincer comprises a rod 20, for example cylindrical, which is guided in translation in the turret 10 by way of suitable guide means 13, for example ball bearings; one of the ends of the rod 20 bears a gripping head—or pincer—consisting of a fixed upper jaw 23 and a lower jaw 25 which is articulated on the rod 20 about a horizontal axis 26. The lower part of the movable jaw 25 bears against the top of the deck 100 in such a way as to keep the pincer closed. The fixed part 23 is provided with a small elastic tongue 24, for example of spring steel, which is arranged obliquely, as can be seen in FIG. 2, and crosses the space separating the fixed 23 and movable 25 parts.

On the top of the gripping head there is additionally fixed a cam control member 27 whose role will be explained hereinbelow; the member 27 is, for example, a welded cylindrical rod.

Along the rod 20, for example on one of the sides of the latter, is fixed a toothing 200 which constitutes a rack; the latter meshes with a pinion 21 integral with a vertical shaft which is guided suitably in the turret 10 (see FIG. 3). The pinion 21 is driven in rotation, in one direction or the other, by a small electrical geared motor 22 mounted on the top of the turret 10. It will be understood that by turning this geared motor in one direction or the other, the rod 20 is displaced along the axis (X—X') in one direction or the other, that is to say by moving the gripping head back in the direction of the turret (retraction) or, in contrast, moving it outwards (extension).

FIG. 4 shows the type of strip which can be used in the measurement unit which is the subject of the invention. The strip (b) is a small elongate rectangle of cardboard or plastic material of low thickness; at the end of the strip, on one of its two faces, there is a zone (z) comprising a substance reactive to glycemia; the particularity of this substance is that of changing color in a continuous manner as a function of the glucose level of the liquid—and in particular of the blood—with which it is impregnated. The change in color makes it possible to determine this glucose level with great precision. There are in fact two distinct reactive zones ($z_1$, $z_2$), which makes it possible to improve still further the precision and reliability of the reading. Strips of this type for glycemia testing are marketed in particular by the company BMP (Boehringer Mannheim Pharma) under the trade name "Haemo-Glukotest".

FIG. 5 shows the station 3 for distribution of strips (b). At this station there is a container 30 which has the shape of a box in which strips (b) ready for use are stored, in a position in which they are stacked one on top of the other.

A weight 34 placed on the stack of strips provides for a certain pressing of the latter against the base 31 of the container. This base is equipped with a distribution roller 33 which preferably has the form of a knurled wheel; the latter is borne on a horizontal shaft 35 which is driven by a small electrical geared motor (not shown). The top of the knurled wheel 33 lies just above the base 31 and bears against the underside of the bottom strip situated in the container 30. The reactive zones, which have not been shown in FIGS. 5 and 5a, are situated at the ends situated towards the right in these figures, and they are facing upwards.

On the left side (where the knurled wheel is situated) there is a small opening 32 which is arranged facing the bottom strip.

FIG. 5a shows how the distribution of a strip from the container 30 to the pincer 2 is effected.

Once the pincer 2 has been positioned, by appropriate rotation of the turret 10, facing the container 30, the pincer 2 is displaced (by starting up the geared motor 22) outwards, so as to arrive at a short distance from the latter. The height of the top of the jaw 25 relative to above (sic) the deck 100 corresponds to the height of the opening 32 relative to this same deck. This approach of the pincer 2 is shown by the arrow ($i_1$) in FIG. 5a. When the pincer 2 is in a suitable position, the geared motor controlling the rotation of the knurled wheel 33 is started up, and the knurled wheel turns in the direction of the arrow ($i_2$). On account of the pressure exerted by the weight 34, the last strip (b) in the stack is driven by friction by the knurled wheel and comes out of the container 30 through the opening 32; its free end then passes under the elastic blade 24 (which gives way) and the strip automatically wedges between the two jaws (arrow $i_3$). The strip is then perfectly secured in the pincer 2, its reactive zone (z) directed outwards and facing upwards.

FIG. 6 shows the station at which a droplet of blood will be deposited on the reactive zone of the strip held by the pincer 2. This station comprises a substantially horizontal support plate 40 which is fixed to the deck 100, by suitable means, by way of a bracket 41. The plate 40 has passing through it a small conduit 42 to which the end of the catheter ($C_1$) is connected. A bearing element 43 having, for example, the form of a small plaque is arranged under the plate 40 and is likewise integral with the bracket 41. Directly below the conduit 42, an opening 430 is provided in the plaque 43, under which opening 430 a small container 44 is arranged. The transporter is designed in such a way that the pincer 2 can bring a strip (b) to the station 4 by positioning the reactive zone (Z) (sic) just below the conduit 42. The presence of the opening 430 prevents soiling of the bearing element 43 in the event of blood arriving in the absence of a strip (b) at station 4.

The wiping station 5 shown in FIG. 7 comprises a fixed frame 51 (borne by the deck 100) which supports an articulated plate 53; on the latter there are mounted two reels, a distributing reel 50 and receiving reel 50' respectively with horizontal axis 500, 500' respectively; this same axis 500' serves advantageously as the articulation for the piece 53 on the frame 51.

The wiping device comprises two pressing blocks, the one a fixed lower pressing block 52 (held by the frame 51), the other a movable upper pressing block 55 (held by the articulated plate 53). On either side of the upper block 55 there are return rollers 56, 56' for a band of absorbent paper (cellulose-based paper). This band—or tape—is unreeled from the reel 50 and reeled onto the reel 50' after passing over the return rollers 56, 56' between the two blocks 55, 52. The receiving reel 50' is driven in rotation by a suitable geared motor 58, which has not been shown in FIG. 7 so as not to complicate it needlessly. The starting up of this geared motor makes it possible to turn the reel 50, in the direction of the arrow ($j_1$) and correlatively to unreel the band of absorbent paper in the direction of the arrows ($j_2$).

On the side facing towards the center of the deck 100, that is to say towards the transporter 1, 2, the plate 53 has a profiled cam 54. The latter has a beveled front edge 540, a substantially horizontal lower part 541, and a beveled rear edge 542. These surfaces are designed to cooperate with the member 27 provided on the top of the pincer 2 in order to bring about the temporary lifting of the plate 53, upon the approach of the pincer charged with a strip, in such a way as to permit positioning of the end of the strip under the band 57 between the pressing blocks 55, 52. This operation will be readily understood from examination of FIG. 8. Once these cam surfaces have been passed, the plate 53 swings downwards under its own weight, and the pressing block 55 applies the band 57 against the zone (z), the strip itself being applied against the lower block 52. Similarly, the withdrawal of the strip is possible by retracting the pincer 2, the rear cam edge 542 then effecting the lifting of the assembly.

FIG. 9 shows the reading station 6 in a plan view. This station is equipped with a case 62 provided with a slot 64 which is facing towards the transporter device and oriented in such a way as to be situated in the trajectory of the strip (b) when the latter is brought to this station. The reading device is a device known per se, for example of the type marketed under the name "REFLOLUX F" (registered trademark) by the company BMP (Boehringer Mannheim Pharma).

The case 62 is held correctly in position on the deck 100 by suitable means such as clamping jaws 65. On this case there is a switch 66 for turning on the reading device.

FIGS. 10 to 12 show the station for removal of the used strip after reading. This station 7 is equipped with an inclined plate 70 provided with a base 71 which is attached to the deck 100. On the top of the plate 70, at a slight distance from the latter and at a level slightly higher than the height of the strip (b) transported by the pincer 2, there is a small retaining tongue 72. An opening 101, for example circular, is provided in the deck 100 just in front of the plate 70. When the pincer 2 has been moved to the ejection station 7 (arrow $l_1$, FIG. 11), the front edge of the strip abuts against the inclined plate 70, and this forces the strip to curve upwards and to pass under the small tongue 72. At the same time, the lower face of the jaw 25 comes into line with the opening 101, and this causes it to swing open (arrow $l_2$). The strip (b) is therefore no longer positively held by the pincer, but is simply bearing against the base of the space separating the two jaws 23, 25. If the pincer 2 is now moved back (arrow $l_3$, FIG. 12), the strip (b) which is braced under the small tongue 72 springs out straight under its own elasticity and leaves the pincer 2; it then falls by gravity through the opening 101 (strip (b') shown in broken lines) into a recovery vessel, or other container 73, advantageously provided under this opening 101.

FIG. 13 shows a so-called "double lumen" catheter especially designed for withdrawal of the blood sample which is to be brought to station 4. Indeed it permits the withdrawal, via the catheter ($C_1$), not of pure blood but of heparinated blood, that is to say a mixture of blood and approximately 10% heparin. The catheter ($C_1$) ends in a hollow body or stopper 9 which is passed through completely by a catheter ($C_3$) of smaller diameter. A catheter 90 designed to be inserted into the vein of the patient is connected to the stopper 9. This catheter 90 surrounds the end 91 of the catheter ($C_3$) and has a length slightly greater than that of this end. The catheters ($C_3$, $C_1$) pass through a single peristaltic pump (P) of known type with two cases, such as, for example, a pump marketed under the trade name ISMATEC. This pump guarantees the slow and regular passage of heparin in the catheter ($C_3$) from a container 92 to the end of the catheter 91 and, simultaneously, the passage of the heparinated blood from the catheter 90 via the stopper 9 and the catheter ($C_1$) to the station 4. It is of course important that the heparin is not injected into the body of the patient, and it is for this reason that the catheter 91 is shorter than the catheter 90. The mixing is carried out immediately after sampling; compared to pure blood, a mixture of this type has the advantage of not coagulating, and this prevents obstruction of the catheters.

The unit for injecting insulin shown in FIG. 14 comprises a support casing 8, likewise mounted on the deck 100. On the top of this casing there is a semicylindrical cradle 86 able to receive a syringe (S) by flush fitting. The latter is filled with insulin at the start of the operation. The device comprises a slide 83 equipped with an adapter 84 able to be snapped onto the plunger head (TS) of the syringe. The slide 83 is integral with a rack 82 housed inside the casing and guided in translation in the latter, parallel to the axis of the syringe. A pinion 81 which is driven by a suitable geared motor (not shown, likewise housed in the casing) makes it possible to displace the rack 82 over a well-defined course and thus to displace the syringe plunger in a corresponding manner, this making it possible to convey a certain dose of insulin to the patient via the catheter ($C_2$).

We will now explain how the artificial pancreas which has just been described is used.

Referring to FIG. 1, the data (d) relating to the patient (M) are first introduced by the therapist into the unit (U). These data are in particular the name, weight, age of the patient, an estimate of his daily subcutaneous insulin requirement, and the glycemia objective which it is desired to attain. Also programmed is the rate at which the samplings will be carried out, for example in the course of one day, as well as the distribution in time of the samplings, it being possible for the rate to be higher at meal times. By way of indication, the samplings can be effected every 7.5 minutes or every 15 minutes. The unit (U) will thus automatically and sequentially control the whole procedure in accordance with the rate and distribution mode selected.

A cycle involving sampling of blood, measurement of glycemia, and injection of insulin takes place in the following manner:

New strips are stored at station 3, and the unit (U) controls the start-up of the geared motors 16 and 22 (see FIG. 2) in such a way as to on the one hand position the turret 10 appropriately so that the axis (X—X') of the pincer 2 is in line with the station 3, and on the other hand to displace the pincer so that it arrives in the proximity of this station (arrow $i_1$, FIG. 5a). At the same time, the knurled wheel 33 is set in rotation so as to deliver a strip (b) which is then gripped by the pincer 2 as has already been explained hereinabove. The transporter is then set in movement again, in such a way that the strip (b), still held by the pincer 2, is brought to the station 4 (see FIG. 6). A little before the arrival of the strip (b) at this station, the peristaltic pump (P) has been put into operation so as to withdraw a little heparinated blood from the arm of the patient. The dose withdrawn is conveyed via the pump into the conduit 42. So as to be certain that the blood arriving in the conduit 42 has just been withdrawn, a certain amount of blood is allowed to pass freely and will not be used in the test. This amount of blood, for example about 15 droplets, was in fact previously in the catheter ($C_1$) and corresponds to a sampling carried out earlier. This unused blood drops into the container 44 by passing through the opening 430 in the bearing element 43. A droplet counter of conventional type is provided (not shown) so that the unit (U) can control the device in such a way that it is a predetermined blood droplet (for example the sixteenth) which drops onto the reactive zone (z) of the strip (b) positioned at station 4. A strip detector of known type, for example opto-electronic is provided, permitting the unit (U) to verify that a strip (b) is in fact present at this station; similarly, a droplet-detector is provided, allowing it to ensure that a droplet does in fact drop onto the reactive zone of the strip. In the event of a fault an error signal is displayed on the screen (E) and an alarm is triggered.

When the blood droplet has been placed on the strip (b), the latter is transferred by the pincer 2 to the wiping station 5 (see FIG. 7). As has already been mentioned hereinabove, the arrival of the pincer at this station causes the lifting of the wiping band 57, so that the zone (z) can take up a position between the pressing blocks 55 and 52; the reel 50' is then set in rotation (arrow $j_1$), which causes a displacement of the paper band 57 (arrow $j_2$) and the wiping of the blood droplet.

It will be noted that the driving of the receiving reel 50' brings about a swinging moment of the plate 53 (arrow $j_3$) which tends to improve the pressing action of the paper band 57 against the strip. This result is obtained by virtue of the fact that the plate 53 is articulated on the same axis 500' as the driving reel 50'. This avoids the use of return springs.

At this point, the solenoid 60 is triggered and acts on the switch on the casing 62 so as to charge the reading device (see FIG. 9). The reading of the color of the reactive zone should be carried out at the end of a predetermined time following wiping, for example one minute. The transporter is thus actuated in such a way as to bring the strip to station 6 in this period of time, the strip being introduced by the movable pincer 2 into the slot 64 of the reading device. The glycemia-reading device has in fact two distinct optical reading systems which evaluate the two reactive zones ($z_1$) and ($z_2$) independently. The results of these measurements are transmitted via line ($L_1$) to unit (U). Once the reading is complete, the strip is extracted from the casing 62, still by the pincer 2, and the turret is set in rotation in the opposite direction so as to return to the station 3 (see FIG. 5) for distribution of new strips. However, on the way, the turret stops in line with the ejection station 7 (see FIG. 10). At this station which, in the embodiment shown, is situated between stations 4 and 5, the used strip is removed, as has already been explained in detail hereinabove with reference to FIGS. 10, 11 and 12.

The pincer 2 thus returns empty to the starting point, that is to say station 3, to wait for the order emanating from the unit (U) for a new cycle.

The results of the reading carried out at station 6 are calculated and analyzed by the unit (U); these results are displayed on the screen (E) and printed on paper by the printer (I) in such a way that the therapist is constantly informed of the development of the situation. The unit (U) moreover calculates the insulin dose which, as a function of the glycemia measurement which has just been effected, is to be administered to the patient. The dose is administered in effect by actuating the geared motor 80 which, by way of the pinion 81 and the rack 82 (see FIG. 14), will displace the plunger of the syringe (S) over a well-defined course.

The artificial pancreas which has just been described is very simple to use and requires a reduced number of personnel. It is very reliable on account of the fact that it uses simple and known components; any malfunctions are easily identifiable and can be quickly corrected. In an advantageous embodiment, all the units constituting this artificial pancreas can be provided on a single support, this support having the appearance of an underframe supporting a data console comprising a keyboard and a screen (monitor). The keyboard, situated in front of the screen, may advantageously consist of a cover articulated on a casing in which is housed the deck 100 and the set of measurement stations, the injection unit (syringe-push) and the peristaltic pump. Thus, in the use position (cover/keyboard closed down on the casing), the set of mechanical components is hidden and protected, while being easily accessible.

A number of variants of the device are of course possible.

Thus, in one of these variants, it would be possible to omit the upper pressing block 55 in the wiping station, the return rollers 56, 56' in this case being designed to cause the paper band to bear as appropriate against the lower block 52.

In the case where the artificial pancreas is intended for injecting glucose, the injection device with syringe and syringe-push is preferably replaced by a peristaltic pump connected to a glucose container. Such a pump in fact makes it possible to administer to the patient relatively high doses of product and therefore to operate at a high dilution (which prevents irritation of the veins by glucose).

Moreover, the artificial pancreas according to the invention could be equipped at one and the same time with a system for insulin injection and a system for glucose injection.

We claim:

1. Artificial pancreas of the type comprising a means for automatically and periodically withdrawing blood samples from the body of a patient (M), means for measuring a level of glucose present in the blood sample (glycemia), means (8) for injecting a dose of insulin or glucose into the body of a patient, and means (u) for calculating and data processing which determines an amount of insulin or glucose to be administered to the patient as a function of the glucose level measured by the measuring means and for controlling the injecting means (8) in a manner corresponding to the amount of insulin or glucose to be administered, characterized in that measurement of glycemia is carried out by reading a color of a reactive zone (z) of a strip (b) reactive to glycemia, the measuring means comprising to this effect:

a) means (3) for distributing strips (b);
b) means (4) for depositing a blood droplet supplied by said withdrawing means on the reactive zone (z) of a strip (b);
c) means (5) for wiping the zone (z);
d) means (6) for optical reading of the color taken by the zone (z);
e) means (7) for removing the strip; and
f) means (1, 2) for automatically conveying the strips (b) individually from means to means (3, 4, 5, 6, 7), wherein said measuring means is mounted on a common deck (100).

2. Artificial pancreas according to claim 1, characterized in that the means for conveying comprises a pincer (2) having an upper jaw (23) and a lower jaw (25) articulated about an axis (26), said jaws (23, 25) being designed to grip and retain a strip (b), said pincer (2) being movably mounted for translation along a substantially horizontal axis (X—X') in a rotary turret (10) rotatable about a vertical axis (Z—Z').

3. Artificial pancreas according to claim 2, characterized in that the upper jaw (23) of said pincer (2) is provided with a small elastic tongue (24) for blocking the strip (b).

4. Artificial pancreas according to claim 2, characterized in that the closure of the pincer (2) being normally ensured by contact between a portion of the lower jaw (25) and a portion of the common deck (100) of the measuring means.

5. Artificial pancreas according to claim 4, characterized in that the means (7) for removing the strip comprises an inclined plate (70) provided with a small tongue (72) for retaining the strip (b), the plate (70) being arranged in the proximity of an opening (101) made in the common deck (100), said opening causing the pincer (2) to open by means of the swinging of the lower jaw (25) and permitting the passage of the removed strips (b').

6. Artificial pancreas according to claim 1, characterized in that the strip distributing means (3) comprises a container (30) in which the strips (b) are positioned horizontally in a vertical stack under a certain pressure, a rotary drive knurled wheel (33) provided level with the base (31) of the container and being designed to remove from the container (30), through an opening (32), a strip adjacent to said opening.

7. Artificial pancreas according to claim 1, characterized in that the depositing means (4) comprises a support plate (40) passed through by a small conduit (42) for delivery of the blood droplet, an element (43), for supporting the strip, arranged under said small conduit (42) and wherein said small conduit is coupled to said withdrawing means (C1,P).

8. Artificial pancreas according to claim 1, characterized in that the wiping means (5) comprises a frame (51) equipped with a pair of reels (50, 50') for distributing and receiving, respectively, a band of absorbent paper (57), means being provided for driving at least one (50') of the reels in rotation, and means for supporting (52) the zone (z) adjacent to said band of absorbent paper (57) and means for selectively pressing (55) the zone (z) into engagement with said band of absorbent paper (57).

9. Artificial pancreas according to claim 8, wherein the means for supporting (52) comprises a lower pressing block (52) and the means for selectively pressing (55) comprises an upper pressing block (55), characterized in that said band (57) is guided by rollers (56, 56') so as to pass between the lower pressing block (52), and the upper pressing block (55), between which the reactive zone of the strip takes up a position.

10. Artificial pancreas according to claim 9, characterized in that said band (57) and the upper pressing block (55) are borne by a plate (53) which is articulated on the frame (51) about a horizontal axis (500'), said plate (53) being integral with a cam (54) for cooperating with a control member (27) equipped on the pincer (2) for temporary lifting of the upper block (55) and the band (57) during the positioning of the reactive zone of the strip between the two blocks (52-55) and during withdrawal of the strip.

11. Artificial pancreas according to claim 1, characterized in that the means (6) for optical reading of the color taken by the reactive zone (z) of the strip (b) comprises a reading casing (62) provided with a slot (64) turned towards the means for conveying (1, 2) and oriented in such a way as to be aligned with the strip (b).

* * * * *

UNITED STATES PATENT AND TRADEMARK OFFICE
CERTIFICATE OF CORRECTION

PATENT NO.   : 5,109,866
DATED        : May 5, 1992
INVENTOR(S)  : Guegan et al.

It is certified that error appears in the above-identified patent and that said Letters Patent is hereby corrected as shown below:

<u>On the cover page:</u>  "[22] PCT Filed: Jul. 22, 1989" should read --[22] PCT Filed: Jul. 20, 1989--

Signed and Sealed this

Thirteenth Day of December, 1994

Attest:

BRUCE LEHMAN

Attesting Officer

Commissioner of Patents and Trademarks